US006861496B2

(12) United States Patent
Kenmoku et al.

(10) Patent No.: US 6,861,496 B2
(45) Date of Patent: Mar. 1, 2005

(54) POLYHYDROXYALKONOATE AND METHOD OF PRODUCING SAME, AND ω-(2-THIENYLSULFANYL) ALKANOIC ACID AND METHOD OF PRODUCING SAME

(75) Inventors: Takashi Kenmoku, Kanagawa (JP); Etsuko Sugawa, Kanagawa (JP); Tetsuya Yano, Kanagawa (JP); Tsuyoshi Nomoto, Tokyo (JP); Takeshi Imamura, Kanagawa (JP); Tomohiro Suzuki, Kanagawa (JP); Tsutomu Honma, Kanagawa (JP)

(73) Assignee: Canon Kabushiki Kaisha, Tokyo (JP)

( * ) Notice: Subject to any disclaimer, the term of this patent is extended or adjusted under 35 U.S.C. 154(b) by 0 days.

(21) Appl. No.: 10/641,090

(22) Filed: Aug. 15, 2003

(65) Prior Publication Data

US 2004/0062811 A1 Apr. 1, 2004

Related U.S. Application Data

(62) Division of application No. 10/084,168, filed on Feb. 28, 2002, now Pat. No. 6,686,439.

(30) Foreign Application Priority Data

| Mar. 1, 2001 | (JP) | .................................... 2001-057085 |
| Feb. 22, 2002 | (JP) | .................................... 2002-046522 |

(51) Int. Cl.⁷ .............................................. C08G 63/02

(52) U.S. Cl. .................... 528/272; 424/78.37; 528/271

(58) Field of Search ...................... 424/78.37; 528/271, 528/272

(56) References Cited

U.S. PATENT DOCUMENTS

| 4,393,167 A | 7/1983 | Holmes et al. ................ 525/64 |
| 4,876,331 A | 10/1989 | Doi ............................ 528/361 |
| 5,135,859 A | 8/1992 | Witholt et al. .............. 435/135 |
| 5,292,860 A | 3/1994 | Shiotani et al. ............. 528/361 |
| 6,645,743 B1 * | 11/2003 | Honma et al. .............. 435/146 |

FOREIGN PATENT DOCUMENTS

| JP | 5-74492 | 1/1993 |
| JP | 5-93049 | 4/1993 |
| JP | 6-15604 | 3/1994 |
| JP | 7-14352 | 2/1995 |
| JP | 7-265065 | 10/1995 |
| JP | 8-19227 | 2/1996 |
| JP | 9-191893 | 7/1997 |
| JP | 2642937 | 8/1997 |
| JP | 2989175 | 12/1999 |
| JP | 2001-178484 | 7/2001 |

OTHER PUBLICATIONS

Fritsche et al., "An unusual bacterial polyester with a phenyl pendant group"; Makromol. Chem. 191, 1957–1965 (1990).

Kim et al., "Preparation and Characterization of Poly(β–hydroxyalkanoates) Obtained from *Pseudomonas oleovorans* Grown with Mixtures of 5–Phenylvaleric Acid and n–Alkanoic Acids"; Macromolecules, 24, 19, 5256–5260 (1991).

Lytle et al., "Filtration Sizes of Human Immunodeficiency Virus Type 1 and Surrogate Viruses Used to Test Barrier Materials"; Applied and Environmental Microbiology, 58, 2, 747–749 (1992).

Ritter et al., "Bacterial production of polyesters bearing phenoxy groups in the side chain, 1"; Macromol. Chem. Phys. 195, 1665–1672 (1994).

Gross et al., "Cyanophenoxy–Containing Microbial Polyesters: Structural Analysis, Thermal Properties, Second Harmonic Generation and In–Vivo Biodegradability"; Polymer International 39, 205–213 (1996).

(List continued on next page.)

*Primary Examiner*—Terressa Boykin
(74) *Attorney, Agent, or Firm*—Fitzpatrick, Cella, Harper and Scinto

(57) ABSTRACT

PHA containing a novel 3-hydroxy-thioalkanoic acid unit having a highly reactive thienyl group in a side chain thereof, and a method of producing the same are provided. Specifically, 5-(2-thienylsulfanyl) valeric acid represented by Chemical Formula [4] below and 6-(2-thienylsulfanyl) hexanoic acid represented by Chemical Formula [5] below are provided. Further, a method of producing PHA, comprising the step of collecting PHA from cells of a microorganism cultured in a medium containing the valeric acid or hexanoic acid, and a novel PHA represented by Chemical Formula [1] below are provided.

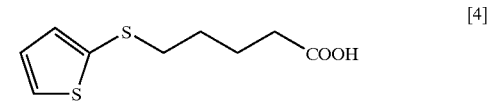

[4]

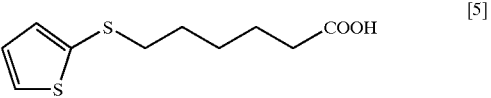

[5]

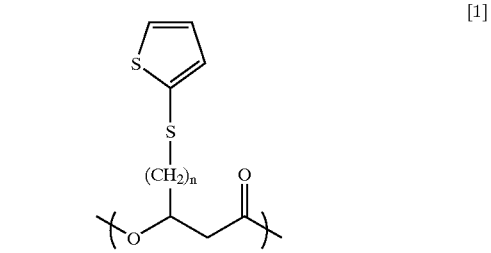

[1]

(n denotes an integer of 1 to 9)

6 Claims, 6 Drawing Sheets

OTHER PUBLICATIONS

Curley et al., "Production of Poly(3–hydroxyalkanoates) Containing Aromatic Substituents by *Pseudomonas oleovorans*"; Macromolecules 29, 1762–1766 (1996).

Park et al., "Epoxidation of Bacterial Polyesters with Unsaturated Side Chains. I. Production and Epoxidation of Polyesters from 10–Undecenoic Acid"; Macromolecules, 31, 5 (1998).

Park et al., "Epoxidation of Bacterial Polyesters with Unsaturated Side Chains. II. Rate of Epoxidation and Polymer Properties"; Polymer Chemistry 36, 2381–2387 (1998).

Aróstegui et al., "Bacterial Polyesters Produced by *Pseudomonas oleovarans* Containing Nitrogen Groups"; Macromolecules 32, 9, 2889–2895 (1999).

Takagi et al., "Biosynthesis of Polyhydroxyalkanoate with a Thiophenoxy Side Group Obtained from *Pseudomonas putida*"; Macromolecules 32, 8315–8318 (1999).

Steinbüchel, et al., "Diversity of bacterial polyhydroxyalkanoic acids", FEMS Microbiology Ltrs., vol. 128, pp. 219–218 (1995).

Jones, et al, "An Asymmetric Synthesis of MK–0417. Observations on Oxazaborolidine–Catalyzed Reductions", J. Org. Chem., vol. 56, pp. 763–769 (1991).

* cited by examiner

| | | |
|---|---|---|
| Mol. Wt.: 116.21 | Mol. Wt.: 209.08 | Mol. Wt.: 244.38 |
| 1 | 2 | 3 |

| 1 | 24.3g | (215mmol) |
|---|---|---|
| $K_2CO_3$ | 45.0g | (323mmol) |
| MIBK | 250ml | |

2  49.4g (237mmol) → DROPPING   HEAT GENERATION 45~58°C

TEMPERATURE RISE  100~110°C

ORANGE→PALE→GREENISH BROWN

REACTION TIME  1.5 HOURS

DILUTION WITH 100ml OF ICE WATER

EXTRACTION WITH TOLUENE → SEPARATION

RECOVERY OF SOLUTION

Y. 54g
YIELD  93.4%

FIG. 2

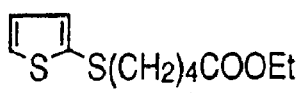 S(CH₂)₄COOEt → 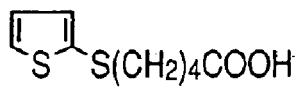 S(CH₂)₄COOH

Mol. Wt.: 244.38              Mol. Wt.: 216.32
        3                              4

| 3          | 54g   | (221mmol) |
|------------|-------|-----------|
| 20%NaOHaq  | 89g   | (442mmol) |
| EtOH       | 260ml |           |

2   49.4g (237mmol) → TEMPERATURE RISE   50~60°C

REACTION TIME   30 MINUTES

↓

DILUTION WITH 600ml OF ICE WATER

6N HClaq → TO PH=1

EXTRACTION WITH TOLUENE →

RINSING → SEPARATION

RECOVERY OF SOLUTION

Y.49g

SILICA-GEL CHROMATOGRAPHY
DECOLORATION WITH CHROMATO-ACTIVE CARBON

RECOVERY OF MAIN FRACTION
Y.39g (LIGHT YELLOWISH VISCOUS LIQUID)
YIELD 83%
Lot.00803
Net.35g

POLYHYDROXYALKONOATE AND METHOD OF PRODUCING SAME, AND ω-(2-THIENYLSULFANYL) ALKANOIC ACID AND METHOD OF PRODUCING SAME

This application is a division of application Ser. No. 10/084,168, filed Feb. 28, 2002, now U.S. Pat. No. 6,686,439.

BACKGROUND OF THE INVENTION

1. Field of the Invention

The present invention relates to a polyhydroxyalkanoate (PHA) as a new type of polyester. The present invention also relates to a method of producing the PHA using a microorganism capable of producing the PHA and accumulating the PHA in its body. The present invention also relates to a compound suitably used for the culture of the microorganism.

2. Related Background Art

Hitherto, many microorganisms have been reported to produce poly-3-hydroxy butyric acid (PHB) and other PHAs and accumulate the same in their bodies ("Biodegradable Plastic Handbook", edited by Biodegradable Plastic Society, NTS Co. Ltd., pp. 178–197 (1995)). These polymers may be used for production of a variety of products using melt processing and the like as with conventional polymers. Furthermore, they have an advantage that they are fully decomposed by microorganisms in the natural world because they are biodegradable, and therefore there are no possibilities that they remain in the natural environment to cause contamination as is the case with many conventional synthetic polymer compounds. Those biodegradable polymer compounds have excellent biocompatibility, and their application as medical soft materials and the like are expected.

It is known that such microorganism-produced PHA may have a variety of compositions and structures depending on the type, culture composition, culture condition and the like of the microorganism for use in the production of the PHA, and studies as to control of such compositions and structures have been conducted mainly in terms of improvement of properties of the PHA.

[1] First, biosynthesized PHAs obtained by polymerizing monomer units having a relatively simple structure such as 3-hydroxy butyric acid (hereinafter abbreviated as 3HB) include:

(a) PHA containing 3HB and 3-hydroxy valeric acid (hereinafter referred to as 3HV).

Japanese Patent Publication No. 6-15604, Japanese Patent Publication No. 7-14352, Japanese Patent Publication No. 8-19227 and Japanese Patent Application Laid-Open No. 5-7492.

(b) PHA containing 3HB and 3-hydroxy hexanoic acid (hereinafter referred to as 3HHx).

Japanese Patent Application Laid-Open No. 5-93049 and Japanese Patent Application Laid-Open No. 7-265065.

(c) PHA containing 3HB and 4-hydroxy butyric acid (hereinafter referred to as 4HB).

Japanese Patent Application Laid-Open No. 9-191893.

(d) PHA containing 3-hydroxy alkanoate having 6 to 12 carbon atoms.

Japanese Patent No. 2642937.

(e) PHA biosynthesized using a single fatty acid as a carbon source. The product is almost the same as (d). Appl. Environ. Microbiol, 58 (2), 746 (1992).

They are all PHA composed of monomer units each having an alkyl group in the side chain, synthesized through β-oxidation of hydrocarbon by a microorganism or synthesis of fatty acid from a sugar, namely "usual PHA".

[2] However, when considering a wider range of application of such microorganism-produced PHA, for example application as a functional polymer, it is expected that PHA having a substituent group other than an alkyl group introduced into the side chain, namely "unusual PHA" will be very useful. Examples of the substituent group include groups containing an aromatic ring (phenyl group, phenoxy group, etc.), unsaturated hydrocarbons, ester group, allyl group, cyano group, halogenated hydrocarbons and epoxide. Among them, in particular, PHA having an aromatic ring have been intensively studied.

(a) PHA having a phenyl group or a partially substituted phenyl group.

It is reported in Macromol. Chem., 191, 1957–1965 (1990) and Macromolecules, 24, 5256–5260 (1991) that using 5-phenyl valeric acid as a matrix, *Pseudomonas oleovorans* produces PHA containing 3-hydroxy-5-phenyl valeric acid as a unit.

It is reported in Macromolecules, 29, 1762–1766 (1996) that using 5-(4'-tolyl) valeric acid as a matrix, *Pseudomonas oleovorans* produces PHA containing 3-hydroxy-5-(4'-tolyl) valeric acid as a unit.

It is reported in Macromolecules, 32, 2889–2895 (1999) that using 5-(2', 4'-dinitrophenyl) valeric acid as a matrix, *Pseudomonas oleovorans* produces PHA containing 3-hydroxy-5-(2', 4'-dinitrophenyl) valeric acid and 3-hydroxy-5-(4'-nitrophenyl) valeric acid as units.

(b) PHA containing a phenoxy group or a partially substituted phenoxy group.

It is reported in Macromol. Chem. Phys., 195, 1665–1672 (1994) that using 11-phenoxy undecylic acid as a matrix, *Pseudomonas oleovorans* produces a PHA copolymer of 3-hydroxy-5-phenoxy valeric acid and 3-hydroxy-9-phenoxy nonanoic acid.

In Japanese Patent No. 2989175 is disclosed an invention relating to a homopolymer composed of 3-hydroxy-5-(monofluorophenoxy) pentanoate (3H5(MFP)P) units or 3-hydroxy-5-(difluorophenoxy) pentanoate (3H5(DFP)P) units, and a copolymer containing at least 3H5(MFP)P units or 3H5(DFP)P units; *Pseudomonas putida* synthesizing these polymers; and a method of producing the above described polymers using a Pseudomonas, and it is described that as an effect thereof, a long-chain fatty acid having a substituent group can be assimilated to synthesize a polymer having a phenoxy group with the end of the side chain substituted with one or two fluorine atoms, and stereoregularity and water repellency can be given while maintaining a high melting point and good processability.

Studies on substances substituted with a cyano group and a nitro group have been conducted in addition to such a substance substituted with a fluorine group.

It is reported in Can. J. Microbiol., 41, 32–43 (1995) and Polymer International, 39, 205–213 (1996) that *Pseudomonas oleovorans* ATCC 29347 and *Pseudomonas putida* KT 2442 strains are used to produce PHA containing 3-hydroxy-p-cyanophenoxy hexanoic acid or 3-hydroxy-p-nitrophenoxy hexanoic acid as a monomer unit using octanoic acid and p-cyanopenoxy hexanoic acid or p-nitrophenoxy hexanoic acid as a matrix.

These reported PHAs each have an aromatic ring as the side chain unlike general PHA having an alkyl group as the side chain, and are useful in obtaining a polymer having properties originating from the PHA.

[3] In addition, as a new category, studies are conducted aimed at producing PHA having a suitable functional group in the side chain, and using the functional group to produce a new function, beyond just changing the properties.

It is reported that Macromolecules, 31, 1480–1486 (1996) and Journal of Polymer Science: Part A: Polymer Chemistry, 36, 2381–2387 (1998) that PHA containing a unit having a vinyl group at the end of the side chain was synthesized, and was thereafter epoxidized with an oxidizing agent, whereby PHA containing an epoxy group having a high reactivity at the end of the side chain could be synthesized.

Also, as an example of synthesis of PHA containing a unit having thioether expected to have a high reactivity, it is reported in Macromolecules, 32, 8315–8318 (1999) that using 11-(phenylsulfanyl) valeric acid as a matrix, *Pseudomonas putida* 27N01 strain produces a PHA copolymer of 3-hydroxy-5-(phenylsulfanyl) valeric acid and 3-hydroxy-7-(phenylsulfanyl) heptanoic acid.

As for the PHA containing a 3-hydroxy-(phenylsulfanyl) alkanoic acid unit having an S atom in the side chain, of the above PHAs, more intensive studies will be expectedly conducted in developing functional PHA in the future in terms of its high reactivity. However, not so many studies have been conducted on this type of PHA, and the reported cases relating to such PHA are only the above described cases. Also, for developing functional PHA by chemically modifying the side chain of obtained PHA, it is desired that the PHA has a side chain having a higher reactivity than a phenyl group, such as for example a thienyl group, but any case of production of such PHA has not yet been reported.

SUMMARY OF THE INVENTION

In view of those problems, an object of the present invention is to provide a novel PHA and a method of producing the same.

The inventors have intensively conducted studies to solve the above-described problems and accomplished the following invention. Specifically, a first aspect of the present invention is polyhydroxyalkanoate itself characterized by having a unit represented by Chemical Formula [1]:

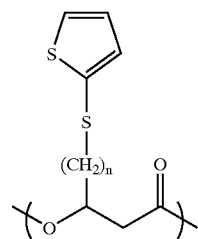

[1]

wherein n denotes an integer of 1 to 9.

Further, the polyhydroxyalkanoate of the present invention is a polyhydroxyalkanoate characterized in that a unit other than the unit represented by Chemical Formula [1] comprises at least one of units represented by Chemical Formula [2]:

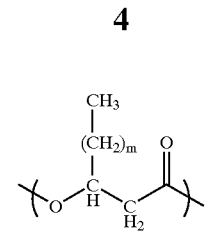

[2]

wherein m denotes an integer of 0 to 8; and Chemical Formula [12]:

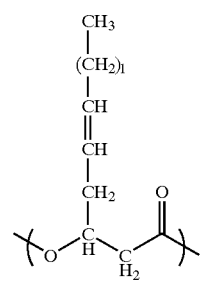

[12]

wherein l denotes 3 or 5.

The polyhydroxyalkanoate obtained by the present invention is a polyhydroxyalkanoate having a number average molecular weight within the range of 10,000 to 1,000,000.

Also, the polyhydroxyalkanoate obtained by the present invention has asymmetric carbon atoms as shown in Chemical Formulas [1], [2] and [12], which accounts for a large number of potential stereoisomers.

However, the production method according to the present invention is characterized in that a microorganism is used to produce polyhydroxyalkanoate, and thus the 3-hydroxyalkanoic acid monomer units are all in R-configuration.

A second aspect of the present invention is a method of producing the above described polyhydroxyalkanoate, characterized in that a microorganism is cultured in a medium containing a compound represented by Chemical Formula [3]:

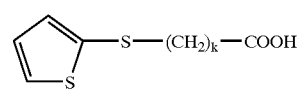

[3]

wherein k denotes an integer of 3 to 11.

More particularly, it is a method of producing a polyhydroxyalkanoate, characterized in that a microorganism is cultured in a medium containing 5-(2-thienylsulfanyl) valeric acid represented by Chemical Formula [4]:

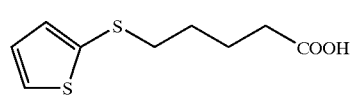

[4]

or 6-(2-thienylsulfanyl) hexanoic acid represented by Chemical Formula [5]:

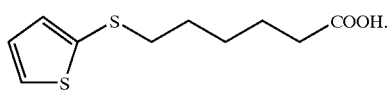

A third aspect of the present invention is ω-(2-thienylsulfanyl) alkanoic acid itself represented by Chemical Formula [11]:

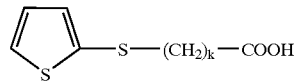

wherein k denotes an integer of 4 to 11, which is required for production of the polyhydroxyalkanoate of the present invention.

The method of producing ω-(2-thienylsulfanyl) alkanoic acid used in the present invention and represented by Chemical Formula [11]:

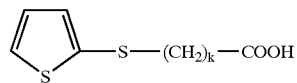

wherein k denotes an integer of 4 to 11, comprises the step of reacting any one of a bromoalkanoic acid, a bromoalkanoic acid ester (referred to as "bromoalkanoate") derivative, a bromoalkanol, a dibromoalkane and a lactone with thiophene-2-thiol.

BRIEF DESCRIPTION OF THE DRAWINGS

FIG. 2 shows a latter part (2/2) of the detailed flowchart for synthesis of 5-(2-thienylsulfanyl) valeric acid in Example 1;

DETAILED DESCRIPTION OF THE PREFERRED EMBODIMENTS

Figure 1:
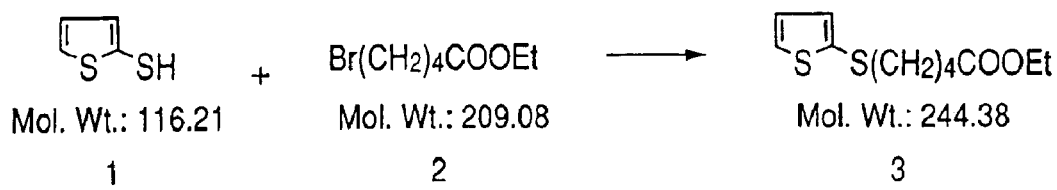
FIG. 1 shows a former part (1/2) of a detailed flowchart for synthesis of 5-(2-thienylsulfanyl) valeric acid in Example 1.

Microorganisms for use in the present invention and processes for culturing the same will be described below.
(Microorganisms)

The microorganism for use in the method of the present invention may be any microorganism that may be cultured in a medium containing ω-(2-thienylsulfanyl) alkanoic acid represented by Chemical Formula [3] to produce a polyhydroxyalkanoate containing a unit represented by Chemical Formula [1], but one example thereof is microorganisms belonging to the Pseudomonas sp. More specifically, those microorganisms include *Pseudomonas cichorii* YN2, FERM BP-7375; *Pseudomonas cichorii* H45, FERM BP-7374; and *Pseudomonas jessenii* P161, FERM BP-7376. These three types of microorganisms are deposited at International Patent Organism Depositary (IPOD) in National Institute of Advanced Industrial Science and Technology (AIST), and described in Japanese Patent Application Laid-Open No. 2001-178484.

There will be given details concerning strains YN2, H45 and P161.

[Bacteriological Properties of Strain YN2]
(1) Morphological Properties

Shape and size of cells: rod, 0.8 μm×1.5 to 2.0 μm
Polymorphism of cells: negative
Mobility: motile
Sporulation: negative
Gram staining: negative
Colony shape: circular; entire, smooth margin; low convex; smooth surface; glossy; translucent (2) Physiological Properties Catalase: positive
Oxidase: positive
0/F test: oxidative (non-fermentative)
Nitrate reduction: negative
Indole production: positive
Acid production from glucose: negative
Arginine dihydrolase: negative
Urease: negative
Esculin hydrolysis: negative
Gelatin hydrolysis: negative
β-Galactosidase: negative
Fluorescent pigment production on King's B agar: positive
Growth under 4% NaCl: positive (weak growth)
Poly-p-hydroxybutyrate accumulation: negative (*)
Tween 80 hydrolysis: positive
(*) Colonies cultured on nutrient agar were stained with Sudan Black for determination.

(3) Substrate Assimilation

Glucose: positive
L-Arabinose: positive
D-Mannose: negative
D-Mannitol: negative
N-Acetyl-D-glucosamine: negative
Maltose: negative
Potassium gluconate: positive
n-Caprate: positive
Adipate: negative
dl-Malate: positive
Sodium citrate: positive
Phenyl acetate: positive

[Bacteriological Properties of Strain H45]
(1) Morphological Properties

Shape and size of cells: rod, 0.8 μm×1.0 to 1.2 μm
Polymorphism of cells: negative
Mobility: motile
Sporulation: negative
Gram staining: negative
Colony shape: circular; entire, smooth margin; low convex; smooth surface; glossy; cream-colored (2) Physiological Properties
- Catalase: positive
- Oxidase: positive
- 0/F test: oxidative
- Nitrate reduction: negative
- Indole production: negative
- Acid production from glucose: negative
- Arginine dihydrolase: negative
- Urease: negative
- Esculin hydrolysis: negative
- Gelatin hydrolysis: negative
- β-Galactosidase: negative
- Fluorescent pigment production on the King's B agar: positive
- Growth under 4% NaCl: negative
- Poly-β-hydroxybutyrate accumulation: negative (3) Ability to Assimilate Substrates
- Glucose: positive
- L-Arabinose: negative
- D-Mannose: positive
- D-Mannitol: positive
- N-Acetyl-D-glucosamine: positive
- Maltose: negative
- Potassium gluconate: positive
- n-Caprate: positive
- Adipate: negative
- dl-Malate: positive
- Sodium citrate: positive
- Phenyl acetate: positive

[Bacteriological Properties of the Strain P161]

(1) Morphological Properties
- Shape and size of cells: spheres, Φ0.6 μm rods, 0.6 μm×1.5 to 2.0 pm
- Polymorphism of cells: elongated form
- Mobility: motile
- Sporulation: negative
- Gram staining: negative
- Colony shape: circle; entire, smooth margin; low convex; smooth surface; pale yellow (2) Physiological Properties
- Catalase: positive
- Oxidase: positive
- 0/F test: oxidative
- Nitrate reduction: positive
- Indole production: negative
- Acid production from glucose: negative
- Arginine dihydrolase: positive
- Urease: negative
- Esculin hydrolysis: negative
- Gelatin hydrolysis: negative
- β-Galactosidase: negative
- Fluorescent pigment production on the King's B agar: positive (3) Substrate Assimilation
- Glucose: positive
- L-Arabinose: positive
- D-Mannose: positive
- D-Mannitol: positive
- N-Acetyl-D-glucosamine: positive
- Maltose: negative
- Potassium gluconate: positive
- n-Caprate: positive
- Adipate: negative
- dl-Malate: positive
- Sodium citrate: positive
- Phenyl acetate: positive (Culture Processes)

For normal culture of a microorganism for use in the method of producing the PHA according to the present invention, for example preparation of a stock strain and multiplication for ensuring the number of cells required for production of PHA and the active state, a culture medium containing components required for multiplication of the microorganism to be used is selected as appropriate. For example, any type of medium such as a general natural medium (bouillon medium, yeast extract, etc.) and a synthetic medium with a nutrient source added therein may be used as long as the growth and survival of the microorganism are not adversely affected. Culture conditions such as temperature, aeration and stirring are selected appropriately depending the microorganism used.

For producing the desired polyhydroxyalkanoate using the PHA-producing microorganism as described above, a basal salt medium containing at least ω-(2-thienylsulfanyl) alkanoic acid represented by the above-mentioned Chemical Formula [3], which corresponds to the monomer unit, and a source of carbon for growth of the microorganism, or the like as a source material required for production of the PHA may be used. It is desirable that the content of the ω-(2-thienylsulfanyl) alkanoic acid in the medium is 0.01 to 1% (w/v), more preferably 0.02 to 0.2%.

The water solubility of the alkanoic acid is not very good, but no problem will be posed even though it is suspended as long as the microorganism of the present invention is used. Also, in some cases, it can be contained in the culture medium in the form of being dissolved or suspended in a solvent such as 1-hexadecene or n-hexadecane. In this case, the concentration of such a solvent in the culture medium solution need to be 3% or less.

For the source of carbon for growth, nutrients such as a yeast extract, polypeptone and a meat extract can be used, and suitable compounds may be selected as appropriate from saccharides, organic acids produced as an intermediate in the TCA cycle and organic acids produced by way of single or double stage biochemical reaction or salts thereof, amino acids or salts thereof, linear alkanoic acids having 4 to 12 carbon atoms or salts thereof in terms of usefulness as a matrix for the strain to be used.

Among them, for saccharides, one or more compounds selected from aldoses, such as glyceroaldehyde, erythrose, arabinose, xylose, glucose, galactose, mannose and fructose,
- alditols such as glycerol, erythritol and xylitol,
- aldonic acids such as gluconic acid,
- uronic acids such as glucuronic acid and galacturonic acid, and
- disaccharides such as maltose, sucrose, lactose and cellobiose.

may suitably be used.

Also, for organic acids or salts thereof, suitable examples include pyruvic acid, oxalacetic acid, citric acid, isocitric acid, ketoglutaric acid, succinic acid, fumaric acid, malic acid and lactic acid, or one or more compounds selected from the salts thereof may suitably be used.

Also, for amino acids or salts thereof, one or more compounds selected from glutamic acid, aspartic acid and salts thereof may suitably be used.

Of these, polypeptone and saccharides are preferably used, and among saccharides, at least one saccharide selected from the group consisting of glucose, fructose and mannose is more preferable. It is desirable that the content of these matrixes in each culture medium is usually preferably 0.1 to 5% (w/v), more preferably 0.2% to 2%.

For one example, the microorganism is cultured in an inorganic medium containing about 0.1 to 5.0% of D-glucose and about 0.01 to 1.0% of ω-(2-thienulsulfanyl) alkanoic acid represented by Chemical Formula [3], or the like, and cells are collected during the period from the logarithmic growth phase to the stationary phase, whereby desired PHA can be extracted. The same amount of yeast extract may be provided in stead of D-glucose.

For the method of making the microorganism produce and accumulate the PHA, productivity may be improved if the sufficient growth of the microorganism is completed, followed by moving the cells to another medium with the content of nitrogen sources such as ammonium chloride limited to a low level, and further culturing the microorganism with compounds forming a desired matrix having a desired unit. Specifically, a multistage method having the above-mentioned processes connected in a multiple stage can be adopted. For example, there is a method in which the microorganism is cultured in an inorganic medium containing about 0.1 to 5.0% of D-glucose and about 0.01 to 10% of ω-(2-thienulsulfanyl) alkanoic acid represented by Chemical Formula [3], or the like, during the period from the logarithmic growth phase to the stationary phase, and the cells are collected by centrifugal separation or the like, followed by further culturing the microorganism in an inorganic medium containing about 0.01 to 10% of ω-(2-thienulsulfanyl) alkanoic acid represented by Chemical Formula [3], with the content of nitrogen sources limited to a low level or almost zero.

The culture temperature may be any temperature allowing the above-described strain to be suitably grown, and an appropriate temperature is, for example, 15 to 40° C., preferably 20 to 35° C. and more preferably 20 to 30° C.

Any culture method, such as liquid culture and solid culture, allowing the microorganism to be grown and to produce the PHA may be used for the culture. In addition, any type of culture may be used including batch culture, fed-batch culture, semi-continuous culture and continuous culture. For the form of the liquid culture, there are a method in which vibration is made with a vibration flask to supply oxygen, and a method of supplying oxygen using a stirring aeration system by a jar fermenter.

The basal salt medium for use in the above-described method may be any medium containing components required for growth of the microorganism such as a source of phosphorus (e.g., phosphate, etc.), a source of nitrogen (e.g., ammonium salt, nitrate, etc.) and the like, and examples of such medium include, for example, an MSB culture medium and an M9 culture medium.

The composition of the mineral culture medium (M9 culture medium) used in one method of the present invention is as follows.

[M9 Culture Medium]

| | |
|---|---|
| $Na_2HPO_4$ | 6.2 g |
| $KH_2PO_4$ | 3.0 g |
| NaCl | 0.5 g |
| $NH_4Cl$ | 1.0 g |

(per liter of medium, pH 7.0)

In addition, for favorable growth and production of PHA, it is necessary to add about 0.3% (v/v) of a minor component solution shown below.

[Minor Component Solution]
nitrilotriacetic acid: 1.5; $MgSO_4$: 3.0;
$MnSO_4$: 0.5; NaCl: 1.0; $FeSO_4$: 0.1;
$CaCl_2$: 0.1; $CoCl_2$: 0.1; $ZnSO_4$: 0.1;
$CuSO_4$: 0.1; $AlK(SO_4)_2$: 0.1;
$H_3BO_3$: 0.1; $Na_2MoO_4$: 0.1; $NiCl_2$: 0.1
(per liter of medium, pH 7.0)

For obtaining the PHA from the culture solution according to the present invention, a method that is usually used may be applied. A method in which a PHA is extracted from the culture solution and purified is used if the PHA is secreted into the culture solution, and a method in which a PHA is extracted from the cells and purified is used if it is accumulated in the cells. For example, for collection of the PHA from cultured cells of the microorganism, extraction by an organic solvent such as chloroform, which is usually carried out, is the most convenient, but dioxane, tetrahydrofuran, acetonitrile or acetone may be used instead of chloroform. In addition, in an environment where use of any organic solvent is not preferred, a method can be adopted in which cell components other than the PHA are removed through treatment with a surface active agent such as SDS, treatment with an enzyme such as lysozyme or treatment with a reagent such as EDTA to remove components in the cell, thereby collecting the PHA alone.

(Carboxylic Acid Derivatives)

For the carboxylic acid derivative for use in the present invention, ω-(2-thienylsulfanyl) alkanoic acid represented by Chemical Formula [3] is used. Among the carboxylic acid derivatives, ω-(2-thienylsulfanyl) alkanoic acid represented by Chemical Formula [11] is a novel compound.

The methods of producing ω-(2-thienylsulfanyl) alkanoic acid with k=ω(ω denotes an integer of 4 to 11) in Chemical Formula [11] include the following.

1-1. Method in which thiophene-2-thiol is reacted with ω-bromo alkanoic acid to obtain ω-(2-thienylsulfanyl) alkanoic acid represented by Chemical Formula 11.

1-2. Method in which thiophene-2-thiol is reacted with ω-bromo alkanoic acid ester (referred to as "alkanoate") to synthesize ω-(2-thienylsulfanyl) alkanoate, followed by hydrolyzing the ester, thereby obtaining ω-(2-thienylsulfanyl) alkanoic acid represented by Chemical Formula [11].

1-3. Method in which thiophene-2-thiol is reacted with ω-bromo-1-alkanol to synthesize ω-(2-thienylsulfanyl)-1-alkanol, followed by oxidizing the same, thereby obtaining ω-(2-thienylsulfanyl) alkanoic acid represented by Chemical Formula [11].

1-4. Method in which thiophene-2-thiol is reacted with 1,ω-dibromoalkane to synthesize 2-[(ω-bromoalkyl) sulfanyl] thiophene, followed by preparing a Grignard reagent using metallic magnesium, and adding carbon dioxide gas, thereby obtaining ω-(2-thienylsulfanyl) alkanoic acid represented by Chemical Formula [11].

1-5. Method in which thiophene-2-thiol is reacted with a lactone to obtain ω-(2-thienylsulfanyl) alkanoic acid represented by Chemical Formula [11].

The above described methods will be more specifically described.

First, methods for producing 5-(2-thienylsulfanyl) valeric acid represented by Chemical Fomula [4] be described below.

2-1. Method in which thiophene-2-thiol is reacted with 5-bromo valeric acid to obtain 5-(2-thienylsulfanyl) valeric acid represented by Chemical Formula [4].

2-2. Method in which thiophene-2-thiol is reacted with 5-bromo valerate to synthesize 5-(2-thienylsulfanyl) valerate, followed by hydrolyzing the ester, thereby obtaining 5-(2-thienylsulfanyl) valeric acid represented by Chemical Formula [4].

2-3. Method in which thiophene-2-thiol is reacted with 5-bromo-1-pentanol to synthesize 5-(2-thienylsulfanyl)-1-pentanol, followed by oxidizing the same, thereby obtaining 5-(2-thienylsulfanyl) valeric acid represented by Chemical Formula [4].

2-4. Method in which thiophene-2-thiol is reacted with 1,4-dibromobutane to synthesize 2-[(4-bromobutyl) sulfanyl] thiophene, followed by preparing a Grignard reagent using metallic magnesium, and adding carbon dioxide gas, thereby obtaining 5-(2-thienylsulfanyl) valeric acid represented by Chemical Formula [4].

2-5. Method in which thiophene-2-thiol is reacted with δ-valerolactone to obtain 5-(2-thienylsulfanyl) valeric acid represented by Chemical Formula [4].

Methods for producing 6-(2-thienylsulfanyl) hexanoic acid represented by Chemical Formula [5] will now be described below.

3-1. Method in which thiophene-2-thiol is reacted with 6-bromo hexanoic acid to obtain 6-(2-thienylsulfanyl) hexanoic acid represented by Chemical Formula [5].

3-2. Method in which thiophene-2-thiol is reacted with 6-bromo hexanoate to synthesize 6-(2-thienylsulfanyl) hexanoate, followed by hydrolyzing the ester, thereby obtaining 6-(2-thienylsulfanyl) hexanoic acid represented by Chemical Formula [5].

3-3. Method in which thiophene-2-thiol is reacted with 6-bromo-1-hexanol to synthesize 6-(2-thienylsulfanyl)-1-hexanol, followed by oxidizing the same, thereby obtaining 6-(2-thienylsulfanyl) hexanoic acid represented by Chemical Formula [5].

3-4. Method in which thiophene-2-thiol is reacted with 1,5-dibromopentane to synthesize 2-[(5-bromopentyl) sulfanyl] thiophene, followed by preparing a Grignard reagent using metallic magnesium, and adding carbon dioxide gas, thereby obtaining 6-(2-thienylsulfanyl) hexanoic acid represented by Chemical Formula [5].

3-5. Method in which thiophene-2-thiol is reacted with ε-caprolactone to obtain 6-(2-thienylsulfanyl) hexanoic acid represented by Chemical Formula [5].

Furthermore, the culture of microorganisms according to the present invention, the production of the PHA and the accumulation of the PHA in cells by the microorganism according to the present invention, the collection of the PHA from the cells in the present invention, and the production of the carboxylic acid derivative represented by Chemical Formula [11] are not limited to the above described methods.

The examples will be described below. Furthermore, "%" found in the following description refers to weight percentage unless otherwise specified.

EXAMPLES

Example 1

Synthesis of 5-(2-thienylsulfanyl) Valeric Acid

Figure 3:
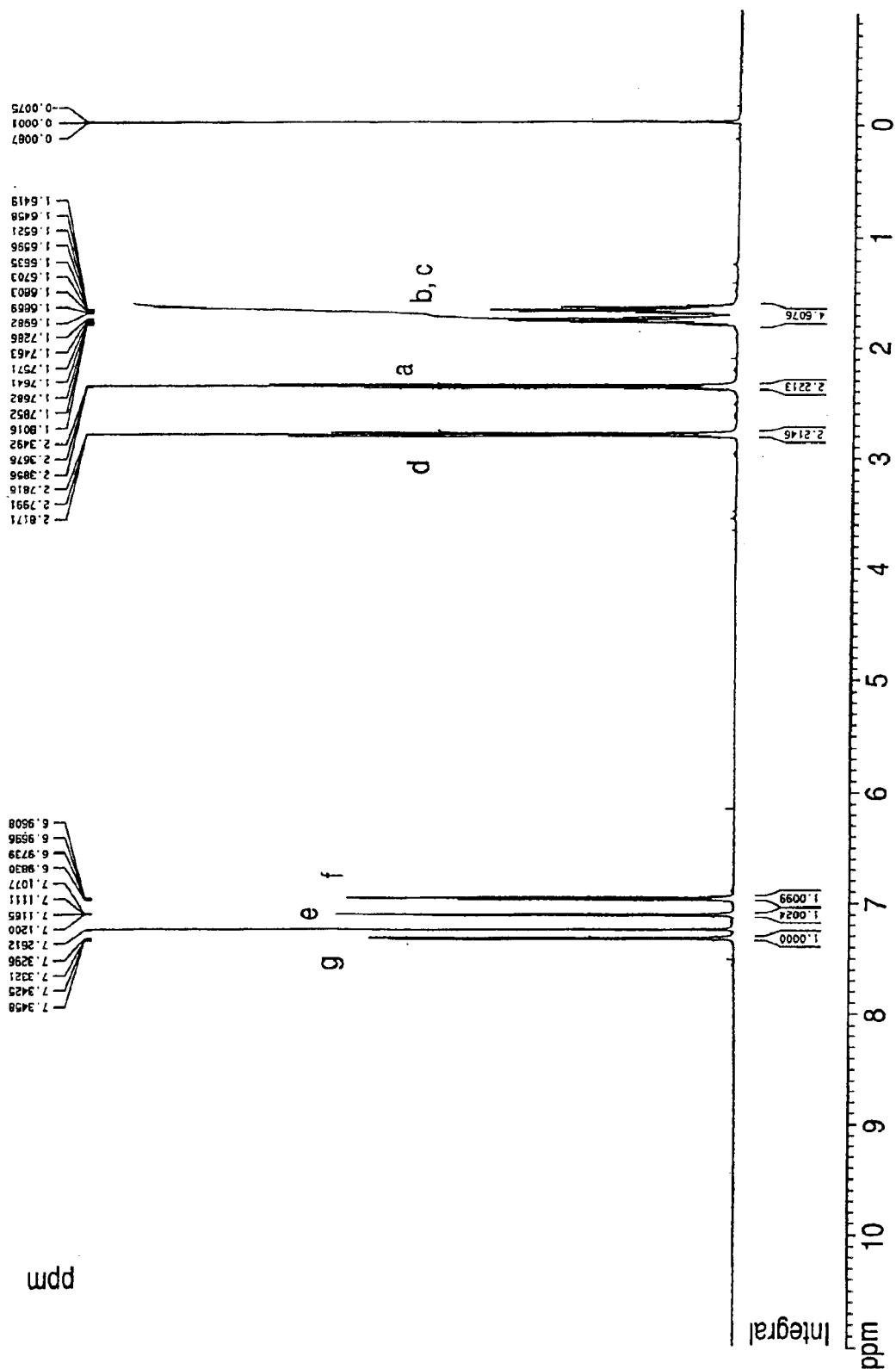
FIG. 3 shows a $^1$H-NMR spectrum of 5-(2-thienylsulfanyl) valeric acid obtained in Example 1.

For synthesis of 5-(2-thienylsulfanyl) valeric acid, thiophene-2-thiol was reacted with ethyl 5-bromovalerate to synthesize ethyl 5-(2-thienylsulfanyl) valerate, and thereafter the ethyl ester at its end was hydrolyzed, thereby obtaining the 5-(2-thienylsulfanyl) valeric acid. For details of the reaction, the reaction was carried out in accordance with the synthesis flow sheets shown in FIGS. 1 and 2. 39 g of 5-(2-thienylsulfanyl) valeric acid was collected from 24.3 g of thiophene-2-thiol, and the yield was 83%. The structure of the obtained 5-(2-thienylsulfanyl) valeric acid was determined by $^1$H-NMR (FT-NMR: Bruker DPX400; $^1$H resonance frequency: 400 MHz; measured nuclear species: $^1$H; used solvent: CDCl$_3$; reference: capillary contained TMS/CDCl$_3$; measuring temperature: room temperature). The $^1$H-NMR spectrum chart is shown in FIG. 3. In addition, the assignment of each hydrogen atom shown in Chemical Formula [6] below is shown in Table 1 ($^1$H-NMR)

TABLE 1

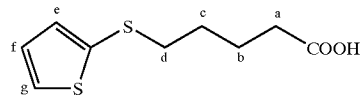

[6]

Result of Assignment of $^1$H-NMR

| ppm | Integrated Value | Fission | Assignment |
| --- | --- | --- | --- |
| 1.64–1.80 | 4H | m | b, c |
| 2.35–2.39 | 2H | t | a |
| 2.78–2.82 | 2H | t | d |
| 6.96–6.98 | 1 | d, t | f |
| 7.11–7.12 | 1 | d, d | e |
| 7.33–7.35 | 1H | d, d | g |

Example 2

Synthesis of 6-(2-thienylsulfanyl) Hexanoic Acid 240 mL of dehydrated acetone was placed in a quadruple ported round flask, and 15.21 g (0.11 mol) of potassium carbonate was added thereto, followed by stirring in a nitrogen atmosphere. To this solution were added 9.00 g (0.06 mol) of sodium iodide and 8.14 g (0.07 mol) of thiophen-2-thiol, followed by stirring adequately in a nitrogen atmosphere at room temperature. Further, 13.39 g (0.06 mol) of ethyl 6-bromohexanoate was added thereto, followed by carrying out heat reflux at 65° C. for 19 hours.

After the reaction, acetone was evaporated using a rotary evaporator, extraction was carried out with chloroform, water was added to separate the solution into phases, and the organic phase was dehydrated with anhydrous magnesium sulfate, followed by evaporating the chloroform using a rotary evaporator, and drying by a vacuum pump to obtain 17.56 g of crude ethyl 6-(2-thienylsulfanyl) hexanoate.

The thus obtained crude ethyl 6-(2-thienylsulfanyl) was subjected to the following hydrolysis reaction without being purified. 17.56 g of the obtained crude ester was dissolved in 300 mL of ethanol-water mixture (1:9 (V/V)), and 10-fold mol of potassium hydroxide was added thereto to carry out a reaction in an ice bath for 4 hours.

The reaction solution was poured in about 2L of 0.1M aqueous hydrochloric acid solution to effect acidification. Extraction was carried out with toluene, and the organic phase was dehydrated with anhydrous magnesium sulfate, followed by evaporating toluene using a rotary evaporator. The thus obtained crude 6-(2-thienylthio) hexanoic acid was purified by silica gel column chromatography (developing solvent: chloroform:methanol=20:1) to obtain 7.21 g of 6-(2-thienylsulfanyl) hexanoic acid.

The overall yield was 52.2% on the basis of ethyl 6-bromohexanoate.

Figure 4:
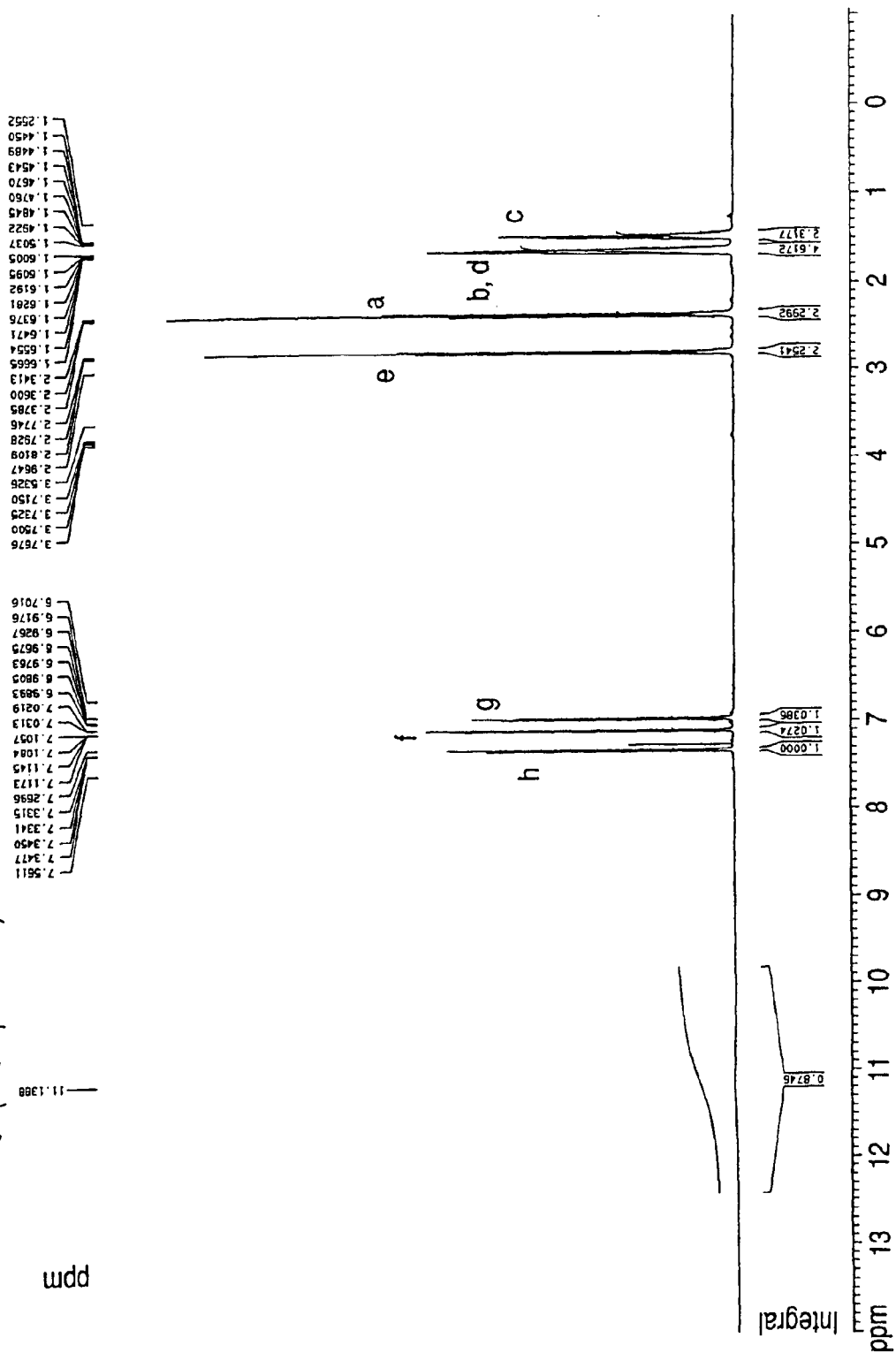
FIG. 4 shows a $^1$H-NMR spectrum of 6-(2-thienylsulfanyl) hexanoic acid obtained in Example 2.

The structure of the obtained 6-(2-thienylsulfanyl) hexanoic acid was determined by $^1$H-NMR (FT-NMR: Bruker DPX400; $^1$H resonance frequency: 400 MHz; measured nuclear species: $^1$H; used solvent: CDCl$_3$; reference: capillary contained TMS/CDCl$_3$; measuring temperature: room temperature). The $^1$H-NMR spectrum chart is shown in FIG. 4. Further, assignment of each hydrogen atom shown in Chemical Formula [7] below is shown in Table 2 ($^1$H-NMR).

TABLE 2

[7]

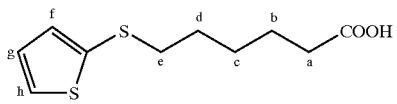

Result of Assignment of $^1$H-NMR

| ppm | Integrated Value | Fission | Assignment |
|---|---|---|---|
| 1.47 | 2H | m | c |
| 1.63 | 4H | m | b, d |
| 2.36 | 2H | t | a |
| 2.79 | 2H | t | e |
| 6.98 | 1H | d, t | g |
| 7.11 | 1H | d, d | f |
| 7.34 | 1H | d, d | h |

Example 3

A colony of YN2 strain on an agar plate was inoculated in 200 mL of M9 culture medium containing 0.5% of polypeptone and 0.1% of 5-(2-thienylsulfanyl) valeric acid obtained in Example 1, and was cultured in a 500 ml volume vibrating flask at 30° C. for 30 hours. After the culture, the cells were harvested by centrifugal separation and cleaned by methanol, and were thereafter freeze-dried. The dried cells were weighed, followed by adding chloroform thereto and stirring for 72 hours at room temperature (about 23° C.), thereby extracting a polymer. The chloroform having the polymer extracted thereinto was filtered and concentrated by an evaporator, followed by collecting precipitated and solidified parts by cool methanol and drying the same at a reduced pressure to obtain the desired polymer. The weight of the dried cells was 153 mg, and the weight of the obtained polymer was 92 mg.

The molecular weight of the obtained polymer was measured by gel permeation chromatography (GPC) (Tosoh HLC-8220 GPC, column: Tosoh TSK-GEL Super HM-H, solvent: chloroform, polystyrene equivalent). For the obtained polymer, the result was Mn=196,000 and Mw=570,000.

Figure 5:
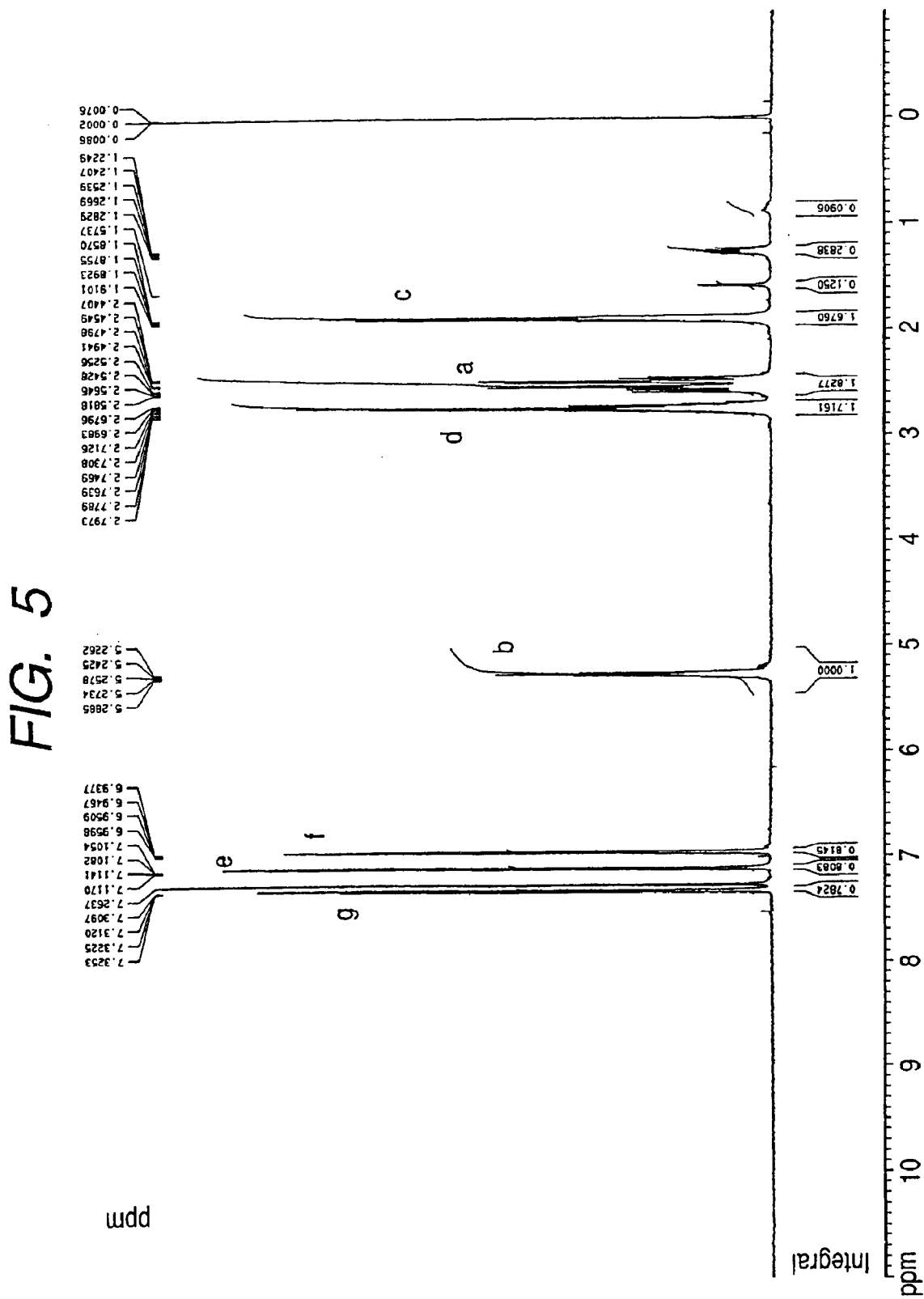
FIG. 5 shows a $^1$H-NMR spectrum of a polymer obtained in Example 3.

The structure of the obtained polymer was determined by $^1$H-NMR (FT-NMR: Bruker DPX400; $^1$H resonance frequency: 400 MHz; measured nuclear specie: $^1$H; used solvent: CDCl$_3$; reference: capillary contained TMS/CDCl$_3$; measuring temperature: room temperature). The $^1$H-NMR spectrum chart is shown in FIG. 5. Further, assignment of each hydrogen atom shown in Chemical Formula [8] below is shown in Table 3 ($^1$H-NMR).

TABLE 3

[8]

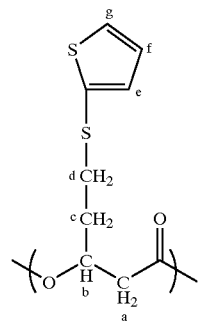

Result of Assignment of $^1$H-NMR

| ppm | Integrated Value | Fission | Assignment |
|---|---|---|---|
| 1.86–1.91 | 2H | m | c |
| 2.44–2.58 | 2H | m | a |
| 2.68–2.80 | 2H | m | d |
| 5.23–5.29 | 1H | m | b |
| 6.94–6.96 | 1H | d, t | f |
| 7.11–7.12 | 1H | d, d | e |
| 7.31–7.33 | 1H | d, d | g |

The result of the assignment of $^1$H-NMR showed that the amount of introduced 3-hydroxy-5-(2-thienylsulfanyl) valeric acid unit as a percentage of that of all components was at least 80%.

Example 4

A colony of YN2 strain on an agar plate was inoculated in 200 mL of M9 culture medium containing 0.5% of glucose and 0.05% of 5-(2-thienylsulfanyl) valeric acid, and was cultured in a 500 ml volume vibrating flask at 30° C. for 45 hours. After the culture, the cells were harvested by centrifugal separation, and were moved to a culture medium prepared by adding 0.5% of glucose and 0.05% of 5-(2-thienylsulfanyl) valeric acid to an M9 culture medium containing no NH$_4$Cl component, where the cells were cultured at 30° C. for 48 hours. After the culture, the cells were harvested by centrifugal separation and cleaned by methanol, and were thereafter freeze-dried. The dried cells were weighed, followed by adding chloroform thereto and extracting a polymer at 60° C. for 24 hours. The chloroform having the polymer extracted thereinto was filtered and concentrated by an evaporator, followed by collecting precipitated and solidified parts by cool methanol and drying the same at a reduced pressure to obtain the desired polymer. The weight of dried cells was 332 mg, and the weight of the obtained polymer was 202 mg.

The molecular weight of the obtained polymer was measured by gel permeation chromatography (GPC) (Tosoh HLC-8220 GPC, column: Tosoh TSK-GEL Super HM-H, solvent: chloroform, polystyrene equivalent). The result was Mn=212,000 and Mw=564,000.

The structure of the obtained polymer was determined by $^1$H-NMR (FT-NMR: Bruker DPX400; $^1$H resonance frequency: 400 MHz; measured nuclear species: $^1$H; used solvent: CDCl$_3$; reference: capillary contained TMS/CDCl$_3$; measuring temperature: room temperature). The result showed that the amount of introduced 3-hydroxy-5-(2-thienylsulfanyl) valeric acid unit as a percentage of that of all components was at least 89%.

Example 5

A polymer was obtained using the procedure of Example 4 with the exception that sodium pyruvate was used in place of glucose. The weight of dried cells was 325 mg, and the weight of the obtained polymer was 210 mg. The molecular weight of the obtained polymer was measured by gel permeation chromatography (GPC) (Tosoh HLC-8220 GPC, column: Tosoh TSK-GEL Super HM-H, solvent: chloroform, polystyrene equivalent). The result was Mn=260,000 and Mw=763,000.

The structure of the obtained polymer was determined by $^1$H-NMR (FT-NMR: Bruker DPX400; $^1$H resonance frequency: 400 MHz; measured nuclear species: $^1$H; used solvent: CDCl$_3$; reference: capillary contained TMS/CDCl$_3$; measuring temperature: room temperature). The result showed that the amount of introduced 3-hydroxy-5-(2-thienylsulfanyl) valeric acid unit as a percentage of that of all components was at least 91%.

Example 6

A polymer was obtained using the procedure of Example 3 with the exception that the H45 strain was used as a strain. The weight of dried cells was 111 mg, and the weight of the obtained polymer was 52 mg. The molecular weight of the obtained polymer was measured by gel permeation chromatography (GPC) (Tosoh HLC-8220 GPC, column: Tosoh TSK-GEL Super HM-H, solvent: chloroform, polystyrene equivalent). The result was Mn=203,000 and Mw=518,000.

The structure of the obtained polymer was determined by $^1$H-NMR (FT-NMR: Bruker DPX400; $^1$H resonance frequency: 400 MHz; measured nuclear species: $^1$H; used solvent: CDCl$_3$; reference: capillary contained TMS/CDCl$_3$; measuring temperature: room temperature). The result showed that the amount of introduced 3-hydroxy-5-(2-thienylsulfanyl) valeric acid unit as a percentage of that of all components was at least 93%.

Example 7

A polymer was obtained using the procedure of Example 3 with the exception that the P161 strain was used as a strain. The weight of dried cells was 98 mg, and the weight of the obtained polymer was 46 mg. The molecular weight of the obtained polymer was measured by gel permeation chromatography (GPC) (Tosoh HLC-8220 GPC, column: Tosoh TSK-GEL Super HM-H, solvent: chloroform, polystyrene equivalent). The result was Mn=187,000 and Mw=539,000.

The structure of the obtained polymer was determined by $^1$H-NMR (FT-NMR: Bruker DPX400; $^1$H resonance frequency: 400 MHz; measured nuclear species: $^1$H; used solvent: CDCl$_3$; reference: capillary contained TMS/CDCl$_3$; measuring temperature: room temperature). The result showed that the amount of introduced 3-hydroxy-5-(2-thienylsulfanyl) valeric acid unit as a percentage of that of all components was at least 93%.

Example 8

A polymer was obtained using the procedure of Example 3 with the exception that 6-(2-thienylsulfanyl) hexanoic acid was used in place of 5-(2-thienylsulfanyl) valeric acid. The weight of dried cells was 199 mg, and the weight of the obtained polymer was 94 mg. The molecular weight of the obtained polymer was measured by gel permeation chromatography (GPC) (Tosoh HLC-8220 GPC, column: Tosoh TSK-GEL Super HM-H, solvent: chloroform, polystyrene equivalent). The result was Mn=32,000 and Mw=101,000.

Figure 6:
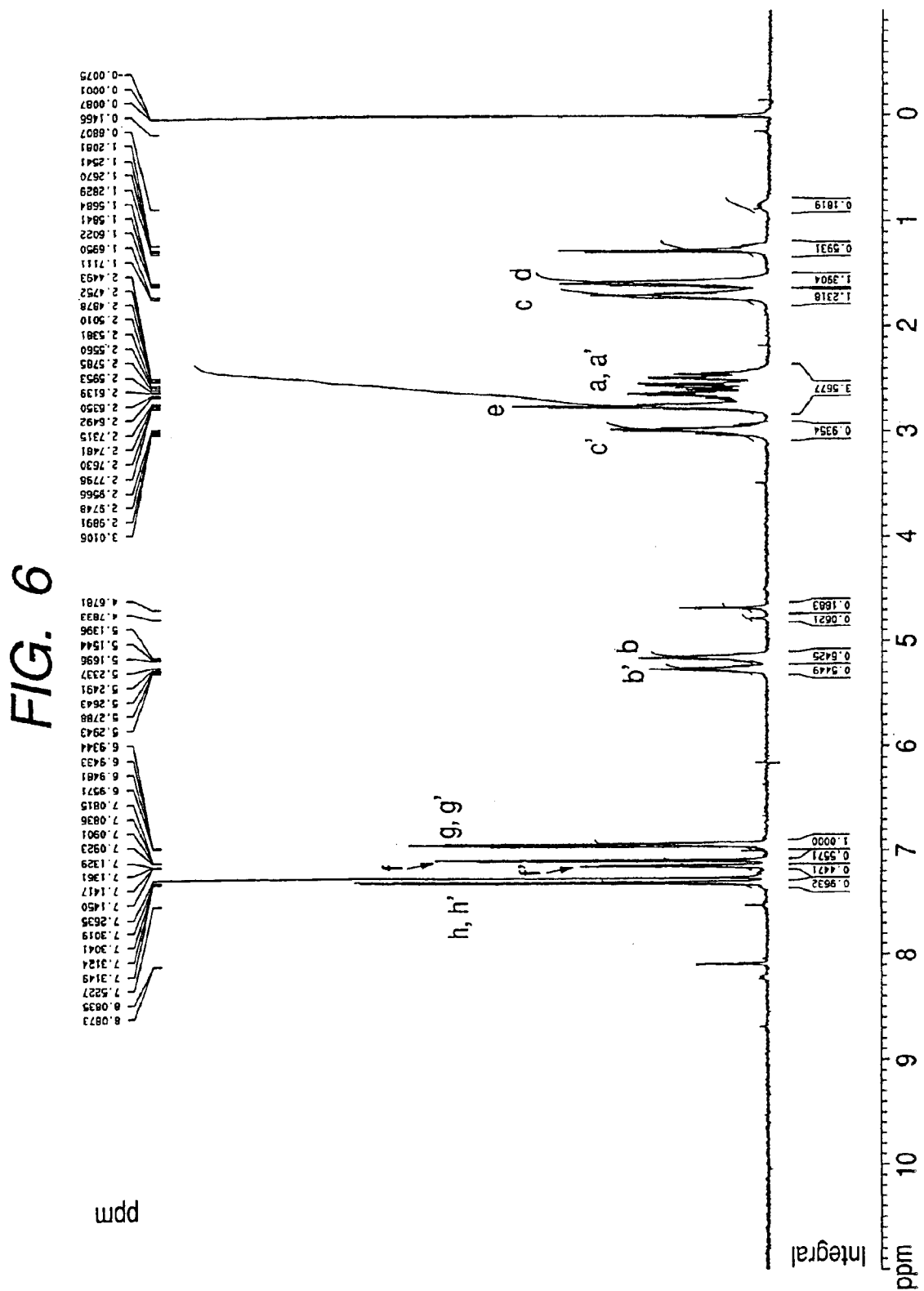
FIG. 6 shows a $^1$H-NMR spectrum of a polymer obtained in Example 8.

Subsequently, $^1$H-NMR measurements were carried out for the obtained polymer (FT-NMR: Bruker DPX400; $^1$H resonance frequency: 400 MHz; measured nuclear species: $^1$H; used solvent: CDCl$_3$; reference: capillary contained TMS/CDCl$_3$; measuring temperature: room temperature). The $^1$H-NMR spectrum chart is shown in FIG. 6. In addition, the assignment of each hydrogen atom shown in Chemical Formulas [9] and [10] below is shown in Table 4 ($^1$H-NMR)

TABLE 4

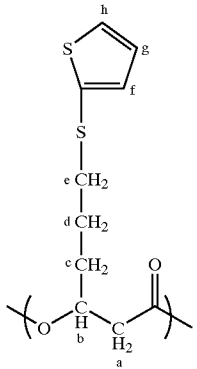

[9]

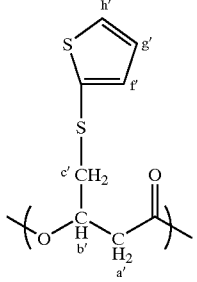

[10]

Result of Assignment of $^1$H-NMR

| ppm | Integrated Value | Fission | Assignment |
|---|---|---|---|
| 1.57–1.71 | 2H | m | c, d |
| 2.45–2.78 | 2H | m | a, a', e |
| 2.96–3.01 | 2H | m | c' |
| 5.14–5.17 | (1H)* | m | b |
| 5.23–5.29 | (1H)* | m | b' |
| 6.93–6.96 | 4H | m | g, g' |
| 7.08–7.09 | (1H)* | t | f |
| 7.13–7.15 | (1H)* | t | f' |
| 7.30–7.31 | 1H | M | h, h' |

*The integrated value increases of decreases depending on the ratio of the above units constiuting the polymer.

The result showed that the amount of introduced 3-hydroxy-6-(2-thienylsulfanyl) hexanoic acid unit as a percentage of that of all components was 46% or more, and the amount of introduced 3-hydroxy-4-(2-thienylsulfanyl) butyric acid unit as a percentage of that of all components was 36% or more.

Example 9

A polymer was obtained using the procedure of Example 4 with the exception that 6-(2-thienylsulfanyl) hexanoic acid was used in place of 5-(2-thienylsulfanyl) valeric acid. The weight of dried cells was 235 mg, and the weight of the obtained polymer was 119 mg. The molecular weight of the obtained polymer was measured by gel permeation chromatography (GPC) (Tosoh HLC-8220 GPC, column: Tosoh TSK-GEL Super HM-H, solvent: chloroform, polystyrene equivalent). The result was Mn=29,000 and Mw=82,000.

The structure of the obtained polymer was determined by $^1$H-NMR (FT-NMR: Bruker DPX400; $^1$H resonance frequency: 400 MHz; measured nuclear species: $^1$H; used solvent: CDCl$_3$; reference: capillary contained TMS/CDCl$_3$; measuring temperature: room temperature). The result showed that the amount of introduced 3-hydroxy-6-(2-thienylsulfanyl) hexanoic acid unit as a percentage of that of all components was 29% or larger, and the amount of introduced 3-hydroxy-4-(2-thienylsulfanyl) butyric acid unit as a percentage of that of all components was 62% or more.

Example 10

A polymer was obtained using the procedure of Example 5 with the exception that 6-(2-thienylsulfanyl) hexanoic acid was used in place of 5-(2-thienylsulfanyl) valeric acid. The weight of dried cells was 215 mg, and the weight of the obtained polymer was 114 mg. The molecular weight of the obtained polymer was measured by gel permeation chromatography (GPC) (Tosoh HLC-8220 GPC, column: Tosoh TSK-GEL Super HM-H, solvent: chloroform, polystyrene equivalent). The result was Mn=37,000 and Mw=109,000.

The structure of the obtained polymer was determined by $^1$H-NMR (FT-NMR: Bruker DPX400; $^1$H resonance frequency: 400 MHz; measured nuclear species: $^1$H; used solvent: CDCl$_3$; reference: capillary contained TMS/CDCl$_3$; measuring temperature: room temperature). The result showed that the amount of introduced 3-hydroxy-6-(2-thienylsulfanyl) hexanoic acid unit as a percentage of all components was 40% or more, and the amount of introduced 3-hydroxy-4-(2-thienylsulfanyl) butyric acid unit as a percentage of that of all components was 49% or more.

Example 11

A polymer was obtained using the procedure of Example 6 with the exception that 6-(2-thienylsulfanyl) hexanoic acid was used in place of 5-(2-thienylsulfanyl) valeric acid. The weight of dried cells was 118 mg, and the weight of the obtained polymer was 33 mg. The molecular weight of the obtained polymer was measured by gel permeation chromatography (GPC) (Tosoh HLC-8220 GPC, column: Tosoh TSK-GEL Super HM-H, solvent: chloroform, polystyrene equivalent). The result was Mn=26,000 and Mw=59,000.

The obtained polymer was subjected to methanolysis in accordance with a conventional procedure, followed by carrying out mass analysis of the polymer by a gas chromatography mass spectrometer (GC-MS, Shimadzu QP-5050, EI Method). As a result, methyl esters were identified of each of 3-hydroxy alkanoic acid units having a linear alkyl chain in the side chain in addition to the 3-hydroxy-6-(2-thienylsulfanyl) hexanoic acid unit and 3-hydroxy-4-(2-thienylsulfanyl) butyric acid unit. The types and area ratios (%) of the monomer units identified by the GC-MS are shown in Table 5.

TABLE 5

| Monomer Unit | Area Ratio |
| --- | --- |
| 3-Hydroxy Butyric Acid | 0.1% |
| 3-Hydroxy Octanoic Acid | 0.2% |
| 3-Hydroxy Decanoic Acid | 0.3% |

TABLE 5-continued

| Monomer Unit | Area Ratio |
| --- | --- |
| 3-Hydroxy-6-(2-Thienylsulfanyl) Butyric Acid | 70.5% |
| 3-Hydroxy-6-(2-Thienylsulfanyl) Hexanoic Acid | 28.9% |

Subsequently, the structure of the obtained polymer was determined by $^1$H-NMR (FT-NMR: Bruker DPX400; $^1$H resonance frequency: 400 MHz; measured nuclear species: $^1$H; used solvent: CDCl$_3$; reference: capillary contained TMS/CDCl$_3$; measuring temperature: room temperature). The result showed that the amount of introduced 3-hydroxy-6-(2-thienylsulfanyl) hexanoic acid unit as a percentage of that of all components was 28% or more, and the amount of introduced 3-hydroxy-4-(2-thienylsulfanyl) butyric acid unit as a percentage of that of all components was 63% or more.

Example 12

A polymer was obtained using the procedure of Example 7 with the exception that 6-(2-thienylsulfanyl) hexanoic acid was used in place of 5-(2-thienylsulfanyl) valeric acid. The weight of dried cells was 93 mg, and the weight of the obtained polymer was 21 mg. The molecular weight of the obtained polymer was measured by gel permeation chromatography (GPC) (Tosoh HLC-8220 GPC, column: Tosoh TSK-GEL Super HM-H, solvent: chloroform, polystyrene equivalent). The result was Mn=23,000 and Mw=46,000.

The structure of the obtained polymer was determined by $^1$H-NMR (FT-NMR: Bruker DPX400; $^1$H resonance frequency: 400 MHz; measured nuclear species: $^1$H; used solvent: CDCl$_3$; reference: capillary contained TMS/CDCl$_3$; measuring temperature: room temperature). The result showed that the amount of introduced 3-hydroxy-6-(2-thienylsulfanyl) hexanoic acid unit as a percentage of that of all components was 21% or more, and the amount of introduced 3-hydroxy-4-(2-thienylsulfanyl) butyric acid unit as a percentage of that of all components was 67% or more.

By the method of the present invention, a novel substance: 5-(2-thienylsulfanyl) valeric acid; a novel substance: 6-(2-thienylsulfanyl) hexanoic acid; and a polyhydroxyalkanoate having a thienyl group in the side chain, and production methods thereof are provided.

What is claimed is:

1. ω-(2-Thienylsulfanyl) alkanoic acid represented by Chemical Formula [11]:

[11]

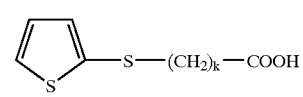

wherein k denotes an integer of 4 to 11.

2. 5-(2-Thienylsulfanyl) valeric acid represented by Chemical Formula [4]:

[4]

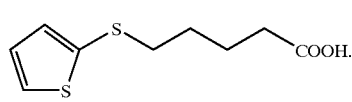

3. 6-(2-Thienylsulfanyl) hexanoic acid represented by Chemical Formula [5]:

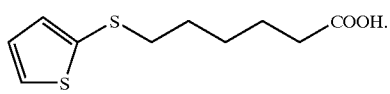

[5]

4. A method of producing ω-(2-thienylsulfanyl) alkanoic acid represented by Chemical Formula [11]:

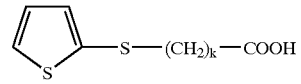

[11]

wherein k denotes an integer of 4 to 11, the method comprising the step of reacting any one of a bromoalkanoic acid, a bromoalkanoate derivative, a bromoalkanol, a dibromoalkane and a lactone with thiophene-2-thiol.

5. The method according to claim 4, wherein any one of the bromoalkanoic acid, bromoalkanoate derivative, bromoalkanol, dibromoalkane and lactone is a compound selected from the group consisting of 5-bromovaleric acid, 5-bromovalerate, 5-bromo-1-pentanol, 1,4-dibromobutane and δ-valerolactone, and 5-(2-thienylsulfanyl) valeric acid represented by Chemical Formula [4] is produced.

6. The method according to claim 4, wherein any one of the bromoalkanoic acid, bromoalkanoate derivative, bromoalkanol, dibromoalkane and lactone is a compound selected from the group consisting of 6-bromohexanoic acid, 6-bromohexanoate, 6-bromo-1-hexanol, 1,5-dibromopentane and ε-caprolactone, and 6-(2-thienylsulfanyl) hexanoic acid represented by Chemical Formula [5] is produced.

* * * * *

UNITED STATES PATENT AND TRADEMARK OFFICE
CERTIFICATE OF CORRECTION

PATENT NO. : 6,861,496 B2  
DATED : March 1, 2005  
INVENTOR(S) : Takashi Kenmoku et al.

It is certified that error appears in the above-identified patent and that said Letters Patent is hereby corrected as shown below:

Title page, Item [54] and Column 1, line 1,
Title, "POLYHYDROXYALKONOATE" should read
-- POLYHYDROXYALKANOATE --.

Title page,
Item [56], References Cited, OTHER PUBLICATIONS,
"Curley et al.," reference, "Substitu nts" should read -- Substituents --.

Column 9,
Line 16, "in stead" should read -- instead --.

Column 10,
Line 63, "be" should read -- will be --.

Column 12,
Table 1, "1     d, t" should read -- 1H     d, t --;
Table 1, "1     d, d" should read -- 1H     d, d --; and
Line 50, "17.56g" should read -- ¶ 17.56g --.

Column 16,
Line 50, "of deceases" should read -- or decreases --.

Signed and Sealed this

Fourteenth Day of February, 2006

JON W. DUDAS  
*Director of the United States Patent and Trademark Office*